United States Patent [19]

af Ekenstam et al.

[11] Patent Number: 4,557,935

[45] Date of Patent: Dec. 10, 1985

[54] GERMICIDAL COMPOSITION

[75] Inventors: Bo T. af Ekenstam, Hjälteby; Per-Olof Glantz, Lund; Kåre Larsson, Bjärred, all of Sweden

[73] Assignee: Biogram AB, Malmö, Sweden

[21] Appl. No.: 613,207

[22] Filed: May 23, 1984

Related U.S. Application Data

[63] Continuation of Ser. No. 441,529, filed as PCT SE82/00061, Mar. 8, 1982, published as WO82/03173, Sep. 30, 1982, § 102(e) date Nov. 4, 1982, abandoned.

[30] Foreign Application Priority Data

Mar. 17, 1981 [SE] Sweden ................................ 8101678

[51] Int. Cl.$^4$ ............................................. A61K 33/40
[52] U.S. Cl. ....................................... 424/130; 514/928
[58] Field of Search ........................................ 424/130

[56] References Cited

U.S. PATENT DOCUMENTS 3,954,974  5/1976  Herzog et al. ...................... 424/130

FOREIGN PATENT DOCUMENTS 1174672  12/1969  United Kingdom .
1372837  11/1974  United Kingdom .

*Primary Examiner*—Leonard Schenkman
*Attorney, Agent, or Firm*—Burns, Doane, Swecker & Mathis

[57] ABSTRACT

A germicidal composition consists of an aqueous suspension of hydrophilic lipid crystals of 1-monolaurin, and preferably also 1-monomyristin, in a quantity of 20-30 percent by weight, and hydrogen peroxide in a quantity of 0.2-5 percent by weight. The hydrophilic lipid crystals stabilize the hydrogen peroxide, to the effect that the composition retains its germicidal power even after having been stored for a long time. Also, the peroxide disintegrates slowly when the composition has been applied onto skin or mucous membrane.

6 Claims, No Drawings

GERMICIDAL COMPOSITION

The present application is a continuation of Ser. No. 441,529, filed as PCT SE82/00061, Mar. 8, 1982, published as WO82/03173, Sep. 30, 1982, § 102(e) date Nov. 4, 1982, now abandoned.

TECHNICAL FIELD

The invention is concerned with a germicidal composition, i.e. a composition that destroys microorganisms. More particularly, the invention is concerned with a germicidal ointment which contains hydrogen peroxide, and which is to be applied to the skin or mucous membrane of man or animals.

BACKGROUND ART

The germicidal power of hydrogen peroxide is well known and is due to the oxidizing effect of the peroxide. The hydrogen peroxide shows a strong tendency of decomposing to form water and molecular oxygen. The rate of decomposition is low at room temperature, provided that the peroxide is absolutely pure. The decomposition can be accelerated by catalysts, such as alkalies, dust particles, and particles having a rough surface. The decomposition strongly reduces the period of time for which a solution of hydrogen peroxide can be stored.

A solution of hydrogen peroxide is rapidly decomposed by peroxidase, when the solution is applied onto a human tissue, such as the skin and the mucous membrane of the mouth. This rapid decomposition results in a germicidal effect of a very short duration. Also, a solution of hydrogen peroxide is considered to have a low power of penetration. These circumstances have strongly reduced the possibility of utilizing the germicidal power of hydrogen peroxide for medical, odontological and dermatological purposes.

SUMMARY OF THE INVENTION

It has now been found that hydrogen peroxide can be effectively stabilized by hydrophilic crystals of 1-monolaurin and 1-monomyristin. The stabilizing effect is so good that the stabilized germicidal composition can be stored for several years without any significant deterioration of the germicidal power.

DESCRIPTION OF THE INVENTION

The germicidal composition of the invention consists of an aqueous suspension containing 20-30 percent by weight of hydrophilic lipid crystals of at least one of the compounds 1-monolaurin and 1-monomyristin, the content of 1-monolaurin being at least 10 percent by weight, and 0.2-5 percent by weight of hydrogen peroxide.

A composition in which the stabilizer merely is 1-monolaurin may cause a slight irritation of the skin or mucous membrane. It has been found that said irritation can be reduced or avoided if 1-monomyristin is substituted for part of the 1-monolaurin. A convenient ratio of 1-monolaurin to 1-monomyristin is from 30:70 to 80:20.

The terms 1-monolaurin and 1-monomyristin are used in this specification and these claims to define a lipid belonging to the group consisting of the 1-monoester of glycerol and lauric acid or myristic acid. In the manufacture of a commercial quality of 1-monolaurin and 1-monomyristin approximately 10% of the 2-isomer is usually formed. The presence of such a quantity of the 2-isomer is no hindrance for the commercial product from being used for the productiion of the germicidal composition of the invention.

The manufacture of hydrophilic lipid crystals of 1-monolaurin and 1-monomyristin has been described in, for example, the British Pat. No. 1,174,672. A dispersion of such lipid crystals is produced by mixing the lipid with water in such a quantity that the water content of the mixture is 50-90 percent by weight, and heating the mixture to a temperature above the conversion temperature, which is considered as the lowest temperature at which lipid particles in contact with an excess of water absorb water and are converted to spherical particles with marked birefringence, known as liposomes. In order to make such of conversion taking place, it is preferred to heat to a temperature 5°-15° C. above conversion temperature. The temperature is now maintained until equilibrium has been achieved, and the mixture is now cooled while stirring, at a cooling rate of 0.5°-5° C. per minute until crystallization occurs and the desired hydrophilic crystals have been formed. Cooling is now continued to room temperature, stirring all the time.

The conversion temperature for 1-monolaurin is about 45° C., and for 1-monomyristin about 50° C.

The hydrophilic lipid crystals produced in this way are thin, leaf-shaped crystals having on their two main surfaces a substantially monomolecular layer in which the polar glycerol end groups face out towards the surface of the crystal. Therefore, the crystal acquires a hydrophilic character.

The hydrophilic crystals of the 1-monoglycerides prepared according to said British Pat. No. 1.174.672 have a surface containing hydroxylic groups in an extremely high density, viz. two hydroxylic groups in approximately 0.23 nm$^2$ (nm=nanometer), vide K. Larsson: Acta Cryst. 21 (1966) 267. An examination of the crystal structure reveals that the outermost atoms are the hydrogen atoms. Therefore, the surface should be a perfect surface for creating hydrogen bonds to oxygen atoms (the hydrogen atoms of the surface are hydrogen donors). Hydrogen peroxide has, contrary to water, a deficit of hydrogen atoms being able to act as hydrogen bond donors. Therefore, it is likely that the molecules of hydrogen peroxide in the aqueous suspension of the invention will show a preference of adhering to the surface of the hydrophilic crystals. Without wanting to commit ourselves to any particular theory, we believe that said adherence is responsible for the very good stabilization of the hydrogen peroxide. This belief is supported by experiments carried out with crystals of 1-monolaurin and 1-monomyristin having a lipophilic surface. Such crystals may be produced by the crystallization of a molten phase. If such lipophilic crystals are in contact with an aqueous solution of hydrogen peroxide, no stabilization of the peroxide can be noticed.

The germicidal composition of the invention has the consistency of an ointment. When the ointment has been applied into the skin or mucous membrane, the hydrogen peroxide starts disintegrating, but the stabilizing effect of the 1-monolaurin and 1-monomyristin ensures a slow disintegration. This means that the ointment retains its germicidal power for a long time. A germicidal power up to six hours after application onto the skin has been noticed. A convenient way of examining the germicidal power is adding potassium iodide to the ointment. If hydrogen peroxide is present, free iodine will be formed.

It has been found, according to the invention. that the 1-monolaurin does not only act as a stabilizer for the hydrogen peroxide, but also increases the germicidal power of the composition. It is a known fact that 1-monolaurin has a bactericidal effect upon Gram-positive bacteria. It appears, however, that the combination of 1-monolaurin and hydrogen peroxide results in synergism, increasing the germicidal power of the composition above that of either component.

The germicidal composition of the invention results in an improved penetration of the hydrogen peroxide into the skin and mucous membrane. A good penetration into the sebaceous glands and the hair follicles is important for the treatment of acne. The composition can be spread onto the skin and mucous membrane to form a thin and stable film. This is important for the treatment of oral ulcers.

The 1-monolaurin and 1-monomyristin are natural components of many foodstuffs. Hydrogen peroxide is produced by certain cells in the human body, and is a normal component of saliva. The components of the composition are allowed as additives to foodstuffs. Consequently, it can be expected that the composition of the invention will be atoxic. Experiments have revealed that this expectation comes true. The composition does not contain components creating allergy.

The composition of the invention can be used as an ointment for wounds and ulcers in general, for example for the treatment of excoriated areas of the groins, bedsores, varicose ulcers, and burns. Zinc ions in the form of a zinc salt may be added to the ointment, for improving and balancing the bacteriocidal effect. The addition of a zinc salt accelerates the healing process beyond that produced by the hydrogen peroxide.

The composition of the invention is also useful in healing inflammations of the soft tissues in the mouth, such as marginal paradontitis, denture sore mouth (prosthetic stomatitis), and various types of oral ulcers, such as aphtoid ulcers, herpes-induced ulcers, angular cheilitis. Clinical experiments have revealed that a treatment with the composition of the invention results in an accelerated healing of acute diseases, such as aphtoid stomatitis, and also results in clear improvements of chronic diseases, such as marginal paradontitis. The composition of the invention has also been found to be non-irritating to the oral tissues.

The composition of the invention is also useful as a prophylactic agent against bacteria in mouth surgery, e.g. in intraoral implantation of metallic articles in the jaw bone.

Another useful area for the composition of the invention is as a body deodorant. The composition does not prevent sweating, but kills effectively the bacteria responsible for the bad smell. The stabilization of the hydrogen peroxide results in a long time action. An antiperspirant can be produced by adding a known astringent agent to the ointment, such as certain metal salts, for example aluminum chloride and aluminum hydroxide.

The composition of the invention is also useful as an emollient to keep the skin soft and elastic. This is particularly helpful to sportsmen, who have often troubles with the skin of the feet, such as thickening of the skin (corn), footsore, fissures and blisters, heavy sweating, and attacks by fungi (epidermophytosis). Salicylic acid can be added to the composition, if a keratolytic effect is desired.

The composition is also useful in veterinary medicine for treating infected wounds, and tissues in danger of being infected. For example, wounds on the tests and udders in bovines, and inflammations in the ear canal in dogs and cats may be treated with the germicidal composition.

The composition of the invention is also useful as a hand cream for persons who have to wash their hands frequently, such as physicians, dentists, veterinarians and other medical practitioners. The hand cream prevents the drying-out of the skin, and creates on the hands a thin layer having bacteriocide properties, which is useful not only for the medical practitioner but also for his patients.

BEST MODE OF CARRYING OUT THE INVENTION, WITH REFERENCE TO EXAMPLES

EXAMPLE 1

1-monolaurin was mixed with 1-monomyristin in the ratio 30:70. 25 parts by weight of said mixture were mixed with 75 parts by weight of distilled water. The mixture was heated to 68° C., and was stirred at said temperature for 15 minutes. The stirring was carried out so as to avoid air being mixed into the mixture. The mixture was now cooled at a cooling rate of 3° C. per minute, the stirring being continued. Crystallization occurred at 30°-35° C. The crystallized suspension was cooled to room temperature, and 6.7 parts by weight of an aqueous solution of hydrogen peroxide were added under continued stirring. The solution contained 30 percent by weight of hydrogen peroxide, resulting in 2 percent by weight of hydrogen peroxide in the finished ointment.

The stirring was continued for another 10 minutes. The ointment was now ready to be packed, for example in tubes.

EXAMPLE 2

An ointment was prepared as described in Example 1, except that 20 parts by weight of the lipid mixture were mixed with 80 parts by weight of distilled water. The finished ointment had a more liquid consistency than that prepared according to Example 1.

EXAMPLE 3

An ointment was prepared as described in Example 1, except that 30 parts by weight of the lipid mixture were mixed with 70 parts by weight of distilled water. The finished ointment had a less liquid consistency than that prepared according to Example 1. Therefore, it was preferred to pack the ointment in medicine bottles or jars.

EXAMPLE 4

20 parts by weight of pulverized 1-monolaurin were mixed with 80 parts by weight of an aqueous solution containing 2.5 percent by weight of hydrogen peroxide. The mixture was heated to 55° C., and was stirred at said temperature until the solid particles had disappeared by forming liquid-crystalline aggregates. The mixture was now cooled, under stirring, at a cooling rate of 1° C. per minute. Crystallization occurred at approximately 30° C. The cooling and stirring was continued until room temperature had been reached. This ointment is useful for being applied onto skin in the final stage of a wound healing process, when the healing wound can accept a slight irritation caused by the 1-monolaurin because of the absence of 1-monomyristin.

EXAMPLE 5

A lipid mixture was prepared, containing ⅓ of 1-monolaurin and ⅔ of 1-monomyristin. 35 parts by weight of this lipid mixture were mixed with 63 parts by weight of distilled water. The mixture was transformed into an ointment base. i.e. an aqueous suspension of hydrophilic lipid crystals, by being heated and cooled in the way described in Example 1. The following ointments were prepared from this ointment base:

A. 98 parts by weight of the ointment base were mixed with 2 parts by weight of hydrogen peroxide.

B. 97 parts by weight of the ointment base were mixed with 3 parts by weight of hexachlorophene.

C. As a comparison, this ointment consisted of the pure ointment base.

Samples of the ointments A, B, and C were placed in small holes in plates of agar gel, to be tested according to the agar diffusion test. The plates were infected with various microorganisms in a quantity of 30 ml per plate according to the standardized test method B1-A. After an incubation period of 20 hours the diameter of the zone of inhibition around each sample was measured. The Table below discloses said diameter, in millimeters:

| Ointment | Staph. aur. | Alc. fac. | Klebs. pneu 10031 | Pseud. aerug | Pseud. sp 8690 | Pseud. sp B10 | Salm. ent | Salm. typhi. |
|---|---|---|---|---|---|---|---|---|
| A | 40 | 23 | 20 | 17 | 12 | 21 | 22 | 20 |
| B | 34 | 12 | 5 | 6 | 6 | 6 | 5 | 0 |
| C | 4 | 0 | 0 | 0 | 0 | 0 | 0 | 0 |

The Table shows that the atoxic ointment A of the invention is superior to the toxic ointment B containing hexachlorophene, which is a widely used germicidal agent.

EXAMPLE 6

The ointment base prepared for Example 5 was used also in this Example. The following ointments A, B, and C were prepared from said ointment base, by the addition of the germicidal agents mentioned below. For comparison, a soap cream D of the trade mark Colga was also tested:

| A: Hydrogen peroxide | 0.5 percent by weight |
| B: Chlorohexidine | 0.5 percent by weight |
| C: 8-oxiquinoline sulphate | 0.5 percent by weight |
| D: Soap cream Colga. | |

These four compositions A-D were tested on five microorganisms in the way described in Example 5. The following Table discloses the diameter of the zones of inhibition:

| Composition | M. aur. | E. coli 7009 | Staph. aur. | Pseud. aureg. | Cand. alb. |
|---|---|---|---|---|---|
| A | 36 | 26 | 39 | 18 | 30 |
| B | 2 | 34 | 2 | 0 | 26 |
| C | 20 | 20 | 22 | 2 | 27 |
| D | 6 | 0 | 6 | 0 | 0 |

The Table shows that the atoxic, non-irritating ointment A of the invention is superior to the ointments B and C, which have a slightly irritating effect on body tissues.

EXAMPLE 7

An ointment was prepared as described in Example 1, except that the ratio of 1-monolaurin to 1-monomyristin was now 60:40. The resulting ointment was comparatively viscous, and was useful for being applied on the mucous membrane of the mouth.

EXAMPLE 8

An ointment was prepared as described in Example 1, except that the ratio of 1-monolaurin to 1-monomyristin was now 80:20. The resulting ointment had a lower viscosity than that of Example 7, and was useful for being applied on infected skin.

EXAMPLE 9

An ointment was prepared as described in Example 1. When the hydrogen peroxide had been added, zinc sulphate was added in a quantity of 0.5 percent by weight. The resulting ointment was useful as a wound healing ointment.

We claim:

1. A germicidal composition consisting essentially of an aqueous suspension containing 20–30 percent by weight of hydrophilic lipid crystals and 0.2–5 percent by weight of hydrogen peroxide, the hydrophilic lipid crystals being 10–100 percent by weight of 1-monolaurin and 0–90 percent by weight of 1-monomyristin.

2. The germicidal composition as claimed in claim 1, wherein the ratio of 1-monolaurin to 1-monomyristin is from 30:70 to 80:20.

3. The germicidal composition as claimed in claim 1, further including a zinc salt.

4. The germicidal composition as claimed in claim 1, further including an astringent agent.

5. The germicidal composition as claimed in claim 1, further including salicylic acid.

6. A method of treating herpes-induced ulcers comprising the application to the ulcers of a germicidal composition as claimed in claim 1.

* * * * *